United States Patent [19]
Brohult et al.

[11] Patent Number: 5,173,511
[45] Date of Patent: Dec. 22, 1992

[54] METHOD FOR TREATMENT OF ALLERGIES USING GLYCEROL ETHERS

[75] Inventors: Sven Brohult; Astrid Brohult, both of Bromma, Sweden

[73] Assignee: Halsoprodukter Lars Karnerud AB, Forserum, Sweden

[21] Appl. No.: 620,380

[22] Filed: Nov. 29, 1990

Related U.S. Application Data

[63] Continuation of Ser. No. 293,943, Jan. 5, 1989, abandoned.

[30] Foreign Application Priority Data

Jan. 21, 1988 [SE] Sweden ............................... 88001821

[51] Int. Cl.$^5$ .............................................. A61K 31/08
[52] U.S. Cl. ..................................... 514/723; 514/722
[58] Field of Search ......................... 514/715, 722, 723

[56] References Cited

U.S. PATENT DOCUMENTS 4,792,555 12/1988 McGregor et al. ................. 514/323

OTHER PUBLICATIONS

Lenhinger, Albert L., "The Molecular Basis of Cell Structure and Function", Biochemistry, 2nd Ed., Worth Publishers, Inc., New York, N.Y., 1975.
Stryer, Lubert, "Biosynthesis of Membrane Lipids and Steroid Hormones", Biochemistry, W. H. Freeman & Co., San Francisco, 1975.
Chem. Abst: 100:174538e, p. 605 (1984), Hyroyuki et al.

Primary Examiner—Frederick E. Waddell
Assistant Examiner—Zohreh A. Fay
Attorney, Agent, or Firm—Cohen, Pontani, Lieberman & Pavane

[57] ABSTRACT

A method for treating a patient to effect the remission of disorders associated with allergies, particularly asthma, by administering to the patient in need of such treatment a glycerol ether in a therapeutically effective amount sufficient to cause remission of such discomfort.

13 Claims, No Drawings

METHOD FOR TREATMENT OF ALLERGIES USING GLYCEROL ETHERS

This is a continuation of U.S. application Ser. No. 07/293,943 filed Jan. 5, 1989, now abandoned.

FIELD OF THE INVENTION

The present invention relates to use of at least one glycerol ether as a compound of a pharmaceutical preparation. The pharmaceutical preparation is for treatment of allergic diseases, especially asthma.

BACKGROUND AND DISCLOSURE OF THE INVENTION

Glycerol ethers (previously also called alkoxyglycerols) have shown several important medical effects. Oral administration of glycerol ether in conjunction with radiation therapy reduces the number of harmful radiation effects: leucopenia and thrombocytopenia are partly or fully prevented. In patients having certain tumor diseases a lower mortality is obtained in a group which has been given glycerol ethers as prophylactic treatment as compared to a group which was not given these substances. Experiments both with humans and animals have shown that the glycerol ethers improve the bodily immunity defense mechanism.

In the human body glycerol ethers are found mainly in bone marrow, liver, mother's milk and placenta. The glycerol ethers are found in larger quantities mainly in shark liver oil.

The glycerol ethers have the following general formula:

$$\begin{array}{l} CH_2.OH \\ | \\ CH.OH \\ | \\ CH_2.O.R, \end{array}$$

wherein R represents a longchained, aliphatic hydrocarbon chain. Naturally occurring glycerol ethers are mixtures with varying number of carbon atoms in the side chain. Compounds having 16 to 18 carbon atoms are present in the largest quantities, but the number of carbon atoms varies mainly with the interval of 14-24. E.g. chimmyl alcohol and batyl alcohol are saturated glycerol ethers having 16 and 18 carbon atoms respectively in the side chain. Selachyl alcohol is an unsaturated glycerol ether with 18 carbon atoms. There also are found methoxysubstituted glycerol ethers, i.e. compounds wherein one hydrogen atom, mostly on carbon atom 2, has been replaced by a methoxy group ($-OCH_3$).

In the human body, like in shark liver oil the glycerol ethers are present as di-esters of fatty acids. They differ from ordinary fat (triglyceride, i.e. a tri-ester of fatty acids) only at one point in the molecule, namely that one of the three ester bonds is replaced by an ether bond.

Diseases, which appear when a person is hyper-sensitive to a foreign substance, are called allergies. These diseases have increased considerably during the latest 20-30 years, perhaps mainly due to the increase of foreign substances in the environment. More than 1 million Swedes have one kind or another of allergy.

It has now unexpectedly been found, that the discomforts caused by several different allergies are greatly reduced by administration of glycerol ethers. Some persons, being hyper-sensitive to certain foods (unsaturated fats, fish, shellfish) have become almost entirely free from the allergic reactions. Especially remarkable is the result obtained in the treatment of asthma. After 3 to 4 months the discomforts start to disappear. In some cases a complete recovery has been observed after 6 months. One case has especially as attracted much interest. That person had had several asthma for 15 years and was totally dependent on various asthma medications (betaprostimulators, broncodilaters, corticosteroids). After 3½ months the discomforts started to disappear. The asthma medications were successively reduced during the subsequent three months and were thereafter completely removed. That person seems now to have fully recovered.

The glycerol ethers have been administered orally using capsules, which are available under the trademark ECOMER. Each capsule contains 0.05 g of the active substance, which comprises a mixture of glycerol ethers and is produced from shark liver.

What is claimed is:

1. A method for treating a patient to effect the reduction of discomfort associated with asthma which comprises administering to the patient in need of such treatment a glycerol mono-ether of a long chained aliphatic hydrocarbon chain in a therapeutically effective amount sufficient to cause the reduction of such disorders.

2. The method of claim 1, wherein the glycerol ether is derived from shark liver oil.

3. The method of claim 1, wherein said glycerol ether contains a straight carbon atom side chain.

4. The method of claim 1, wherein the glycerol is a methoxy-substituted glycerol ether.

5. The method of claim 1, wherein the glycerol ether is a methoxy-substituted ether containing a straight chain atom side chain.

6. A method of treating a subject having asthma, comprising:
administering thereto an effective dose of triglycerol ethers having the following formula:

$$\begin{array}{l} CH_2-O-R^1 \\ | \\ CH-O-R^2 \\ | \\ CH_2-O-R^3 \end{array}$$

wherein
$R^1$ and $R^2$ are each independently selected from the group consisting of hydrogen and acyl radicals, and
$R^3$ is selected from the group consisting of long chain aliphatic hydrocarbon radicals, and methoxy substituted glycerol ethers having a hydrogen atom replaced by a methoxy group, and mixtures thereof.

7. A method according to claim 6 wherein said composition is produced from shark liver oil.

8. A method according to claim 6 wherein $R^3$ is a $C_{14}$-$C_{24}$ aliphatic hydrocarbon.

9. A method according to claim 8 wherein $R^3$ is primarily a $C_{16}$-$C_{18}$ aliphatic hydrocarbon.

10. A method according to claim 9 wherein $R_3$—OH is selected from the group consisting of chimyl alcohol, batyl alcohol and selachyl alcohol.

11. A method according to claim 6 containing 50 mg of active substances.

12. A method according to claim 7 containing 50 mg of active substances.

13. A method for the treatment of asthma comprising the administration to a person having a tendency to suffer from asthma of an effective amount of a pharmaceutical composition containing glycerol mono-ethers of long chained aliphatic hydrocarbon chains derived from the purification of shark liver oil.

* * * * *